(12) United States Patent
Midha

(10) Patent No.: US 6,555,136 B2
(45) Date of Patent: *Apr. 29, 2003

(54) PHARMACEUTICAL DOSAGE FORM FOR PULSATILE DELIVERY OF METHYLPHENIDATE

(75) Inventor: Kamal K. Midha, Hamilton (BM)

(73) Assignee: PharmaQuest, Ltd., Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 09/992,353

(22) Filed: Nov. 13, 2001

(65) Prior Publication Data

US 2002/0058061 A1 May 16, 2002

Related U.S. Application Data

(63) Continuation of application No. 09/544,732, filed on Apr. 6, 2000, now Pat. No. 6,340,476.
(60) Provisional application No. 60/127,984, filed on Apr. 6, 1999.

(51) Int. Cl.⁷ .................................................. A61K 9/26
(52) U.S. Cl. ..................... 424/469; 424/451; 424/452; 424/457; 424/458; 424/459; 424/463; 424/464; 424/465; 424/468; 424/474; 424/475; 424/481; 424/482
(58) Field of Search .......................... 424/451, 452, 424/457, 458, 459, 463, 464, 465, 468, 469, 474, 475, 481, 482

(56) References Cited

U.S. PATENT DOCUMENTS

| | | |
|---|---|---|
| 4,627,850 A | 12/1986 | Deters et al. |
| 4,713,247 A | 12/1987 | Sakamoto et al. |
| 4,728,512 A | 3/1988 | Mehta et al. |
| 4,777,049 A | 10/1988 | Magruder et al. |
| 4,874,388 A | 10/1989 | Wong et al. |
| 4,957,494 A | 9/1990 | Wong et al. |
| 4,971,805 A | 11/1990 | Kitanishi et al. |
| 5,023,088 A | 6/1991 | Wong et al. |
| 5,110,597 A | 5/1992 | Wong et al. |
| 5,204,116 A | 4/1993 | Edgren et al. |
| 5,209,746 A | 5/1993 | Balaban et al. |
| 5,221,278 A | 6/1993 | Linkwitz et al. |
| 5,236,689 A | 8/1993 | Wong et al. |
| 5,260,068 A | 11/1993 | Chen |
| 5,260,069 A | 11/1993 | Chen |
| 5,300,304 A | 4/1994 | Sheth et al. |
| 5,308,348 A | 5/1994 | Balaban et al. |
| 5,312,390 A | 5/1994 | Wong |
| 5,340,590 A | 8/1994 | Wong et al. |
| 5,348,748 A | 9/1994 | Sheth et al. |
| 5,391,381 A | 2/1995 | Wong et al. |
| 5,407,686 A | 4/1995 | Patel et al. |
| 5,445,828 A | 8/1995 | Pozzi et al. |
| 5,456,679 A | 10/1995 | Balaban et al. |
| 5,472,708 A | 12/1995 | Chen |
| 5,498,255 A | 3/1996 | Wong |
| 5,499,979 A | 3/1996 | Wong et al. |
| 5,508,040 A | 4/1996 | Chen |
| 5,531,736 A | 7/1996 | Wong et al. |
| 5,773,478 A | 6/1998 | Richards et al. |
| 5,801,271 A | 9/1998 | Seido et al. |
| 5,837,284 A | 11/1998 | Mehta et al. |
| 5,859,249 A | 1/1999 | Seido et al. |
| 5,874,090 A | 2/1999 | Baker et al. |
| 5,914,129 A | 6/1999 | Mauskop |
| 6,150,376 A | 11/2000 | Kozikowski et al. |
| 6,217,904 B1 * | 4/2001 | Midha et al. ............... 424/468 |
| 6,340,476 B1 * | 1/2002 | Midha et al. ............... 424/469 |

FOREIGN PATENT DOCUMENTS

WO    WO 98/06380    2/1998

OTHER PUBLICATIONS

Conte et al. (2000), "A Flexible Technology for the Linear, Pulsatile and Delayed Release of Drugs, Allowing for Easy Accommodation of Difficult In Vitro Targets," *Journal of Controlled Release* 64:263–268.

* cited by examiner

*Primary Examiner*—Thurman K. Page
*Assistant Examiner*—Liliana Di Nola-Baron
(74) *Attorney, Agent, or Firm*—Dianne E. Reed; Karen Canaan; Reed & Associates

(57) ABSTRACT

Novel pharmaceutical dosage forms provide for pulsatile delivery of methylphenidate, i.e., release encapsulated drug in spaced apart "pulses." The dosage forms are comprised of first, second and optionally third dosage units, with each dosage unit having a different drug release profile. The dosage forms may comprise capsules housing compressed tablets or drug-containing beads or particles, or may comprise a single tablet with the first, second and optionally third dosage units each representing an integral and discrete segment thereof. Methods of treatment using the pharmaceutical dosage forms are provided as well.

45 Claims, No Drawings

PHARMACEUTICAL DOSAGE FORM FOR PULSATILE DELIVERY OF METHYLPHENIDATE

CROSS-REFERENCE TO RELATED APPLICATIONS

This is a continuation of U.S. Ser. No. 09/544,732, filed Apr. 6, 2000, now U.S. Pat. No. 6,340,476, which claims priority under 35 U.S.C. §119(e)(1) to U.S. Provisional Patent Application Serial No. 60/127,984, filed Apr. 6, 1999. The disclosures of the aforementioned patent applications are incorporated by reference in their entireties.

The present invention relates generally to drug delivery, and more specifically relates to novel pharmaceutical dosage forms that provide pulsatile delivery of methylphenidate. The invention additionally relates to methods for administering methylphenidate using the novel dosage forms.

BACKGROUND

Pharmaceutical dosage forms are known which provide a variety of drug release profiles, including immediate release, sustained release, and delayed release. That is, it may be desirable, for a particular drug, to prevent drug release after drug administration until a certain amount of time has passed (so-called "timed release"), to provide substantially continuous release over a predetermined time period (so-called "sustained release") or to provide release immediately following drug administration (i.e., "immediate release"). For some types of drugs, it is preferred to release the drug in "pulses," wherein a single dosage form provides for an initial dose of drug followed by a release-free interval, after which a second dose of drug is released, followed by one or more additional release-free intervals and drug release "pulses." Pulsatile drug delivery is useful, for example, with active agents that have short half-lives and must be administered two or three times daily, with active agents that are extensively metabolized presystemically, and with active agents which lose the desired therapeutic effect when constant blood levels are maintained. These types of agents have pharmacokinetic-pharmacodynamic relationships that are best described by a clockwise "hysteresis loop." A drug dosage form that provides a pulsatile drug release profile is also useful for minimizing the abuse potential of certain types of drugs, i.e., drugs for which tolerance, addiction and deliberate overdose can be problematic.

Because a precise and effective pulsatile drug delivery system is difficult to formulate and manufacture, there are few such dosage forms that have been commercialized. There are, however, several patents and literature references pertaining to pulsatile drug delivery. See, for example, U.S. Pat. No. 5,413,777 to Sheth et al., directed to a pulsatile once-a-day delivery system for the administration of minocycline; U.S. Pat. No. 5,260,068 to Chen, directed to a multiparticulate pulsatile drug delivery system; U.S. Pat. No. 4,777,049 to Magruder et al., directed to an osmotic delivery system for constant release of a drug with intermittent release "pulses"; U.S. Pat. No. 5,391,381 to Wong et al., directed to a drug dispenser for delivering individual drug-containing units in a "pulsatile" manner; PCT Publication No. WO 98/32424, pertaining to pulsatile delivery of diltiazem hydrochloride; U.S. Pat. Nos. 5,472,708 and 5,260,069 to Chen; Ishino et al. (1992) "Design and Preparation of Pulsatile Release Tablet as a New Oral Drug Delivery System," *Chem. Pharm. Bull.* 40(11):3036–3041; Cohen et al. (1994), "Pulsatile Release from Microencapsulated Liposomes," *J. Liposome Res.* 349–360; and Gazzaniga et al. (1994), "Chronotopic Drug Delivery Systems for Pulsatile and/or Site-Specific Release," $21^{st}$. *Proc. Int. Symp. Controlled Release Bioact. Mater.*, pp. 744–745.

The present invention is directed in part to a novel pulsatile drug delivery system which is straightforward to manufacture and provides precisely timed drug release "pulses" at desired intervals.

Methylphenidate hydrochloride (HCl), the hydrochloride salt of α-phenyl-2-piperidine-acetic acid methyl ester (available commercially as Ritalin®), is a central nervous system stimulant that is used in the treatment of Attention Deficit Disorder ("ADD"), a commonly diagnosed nervous system illness in children that is characterized by both distractability and impulsivity. Methylphenidate HCl is also used to treat a related disorder, Attention Deficit Hyperactivity Disorder ("ADHD"), in which symptoms of hyperactivity are present along with the symptoms of ADD. The drug is additionally used in the symptomatic treatment of narcolepsy, depression, and the cognitive decline associated with Acquired Immunodeficiency Syndrome ("AIDS") or AIDS-related conditions, as well as for mood elevation, particularly in terminally ill patients with diseases such as cancer. Methylphenidate exists as four distinct isomers, as follows:

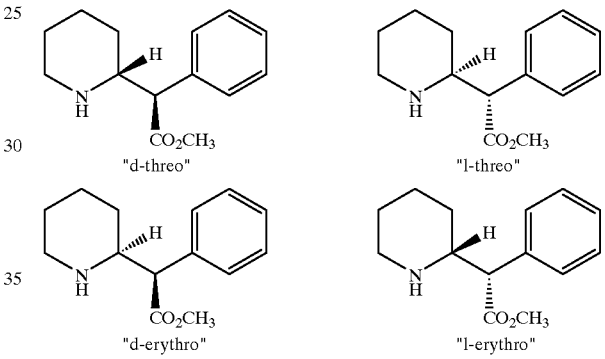

The drug as used in therapy is a racemic mixture of the d- and l-threo enantiomers, which have been acknowledged as more active than the erythro pair.

Because of its potential for tolerance (loss of clinical efficacy when constant blood levels are maintained), short-half life and potential for abuse, methylphenidate is a primary candidate for use in conjunction with the drug delivery systems of the invention.

Accordingly, the present invention provides novel pharmaceutical dosage forms for the administration of methylphenidate in its conventional form, i.e., as a racemic mixture of the d-threo and l-threo enantiomers. The novel dosage forms provide for pulsatile drug release, thereby maximizing efficacy (i.e., the loss of clinical efficacy over time), reducing the potential for abuse or noncompliance. The invention thus represents a significant advance in the art, particularly in the administration of drugs such as methylphenidate that have short half-lives, tend to be extensively metabolized presystemically, have pharmacokinetic-pharmacodynamic relationships which are best described by positive (clockwise) hysteresis loops (hence resulting in tolerance when constant blood levels are maintained), or are likely candidates for drug abuse. No art of which applicants are aware describes pulsatile drug delivery systems as now provided herein.

To the best of applicants' knowledge, the pharmaceutical dosage forms of the invention are previously unknown and completely unsuggested by the art.

SUMMARY OF THE INVENTION

Accordingly, it is a primary object of the invention to address the above-mentioned need in the art by providing a pharmaceutical dosage form for pulsatile delivery of methylphenidate.

It is another object of the invention to provide such a dosage form comprising at least two individual drug-containing dosage units, each of which has a different drug release profile.

It is another object of the invention to provide such a dosage form wherein the dosage units are housed in a closed capsule.

It is still another object of the invention to provide such a dosage form wherein the dosage units are compressed tablets.

It is yet another object of the invention to provide such a dosage form wherein the dosage units are drug-containing particles or beads.

It is a further object of the invention to provide such a dosage form comprised of a single tablet of which the drug-containing dosage units represent integral but discrete segments.

It is a further object of the invention to provide such a dosage form for administering methylphenidate optionally in combination with one or more other active agents such as CNS stimulants (including analeptic agents and psychostimulants), antidepressant drugs, antianxiety agents and the like.

It is an additional object of the invention to provide methods for administering methylphenidate using the novel dosage forms.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

Definitions and Nomenclature

Before the present formulations and methods of use are disclosed and described, it is to be understood that unless otherwise indicated this invention is not limited to specific pharmacologically active agents, specific pharmaceutical carriers, or to particular administration regimens, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an active agent" includes mixtures of active agents, reference to "a pharmaceutical carrier" includes combinations of two or more carriers, and the like.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not.

The terms "active agent," "drug" and "pharmacologically active agent" are used interchangeably herein to refer to a chemical material or compound which, when administered to an organism (human or animal, generally human) induces a desired pharmacologic effect. In the context of the present invention, the terms refer to a compound that is capable of being delivered orally.

The term "methylphenidate" as used herein refers to a racemic mixture of d-threo methylphenidate and l-threo methylphenidate, also referred to herein as "d,l-methylphenidate."

By the terms "effective amount" or "pharmaceutically effective amount" of an agent as provided herein are meant a nontoxic but sufficient amount of the agent to provide the desired therapeutic effect. The exact amount required will vary from subject to subject, depending on age, general condition of the subject, the severity of the condition being treated, and the particular active agent administered, and the like. Thus, it is not possible to specify an exact "effective amount." However, an appropriate "effective" amount in any individual case may be determined by one of ordinary skill in the art using routine experimentation.

By "pharmaceutically acceptable" carrier is meant a carrier comprised of a material that is not biologically or otherwise undesirable, i.e., the material may be administered to an individual along with the selected active agent without causing any undesirable biological effects or interacting in a deleterious manner with any of the other components of the pharmaceutical composition in which it is contained. The term "carrier" is used generically herein to refer to any components present in the pharmaceutical formulations other than the active agent or agents, and thus includes diluents, binders, lubricants, disintegrants, fillers, coloring agents, wetting or emulsifying agents, pH buffering agents, preservatives, and the like.

Similarly, a "pharmaceutically acceptable" salt or a "pharmaceutically acceptable" ester of a compound as provided herein is a salt or ester which is not biologically or otherwise undesirable.

In the chemical structures drawn herein, the use of bold and dashed lines to denote particular conformation of substituents follows IUPAC convention. The symbols "α" and "β" indicate the specific stereochemical configuration of a substituent at an asymmetric carbon atom in a chemical structure as drawn. Thus "α," denoted by a broken line, indicates that the group in question is below the general plane of the molecule as drawn, and "β" denoted by a bold line, indicates that the group at the position in question is above the general plane of the molecule as drawn.

"Pulsatile Release" Dosage Forms

In a first embodiment, the invention features pharmaceutical dosage forms that provide for pulsatile delivery of methylphenidate. By "pulsatile" is meant that a plurality of drug doses are released at spaced apart time intervals. Generally, upon ingestion of the dosage form, release of the initial dose is substantially immediate, i.e., the first drug release "pulse" occurs within 1–2 hours of ingestion. This initial pulse is followed by a first time interval during which substantially no drug is released from the dosage form, after which a second dose is then released. Typically, the second dose is released on the order of 3–5 hours following ingestion of the dosage form. Preferably, release of the second dose is followed by a second non-release interval, which is again followed by a "pulse" of drug release. Ideally, release of a third dose occurs on the order of 7–9 hours following ingestion. In a preferred embodiment herein, either two or three release pulses are provided. However, the invention is also intended to encompass dosage forms that provide more than three pulses, with non-release intervals therebetween of approximately 2–6 hours, preferably 3–5 hours.

The aforementioned pulsatile release profile is achieved with dosage forms that, in one embodiment, are closed and preferably sealed capsules housing two or more drug-containing "dosage units." In a preferred embodiment, each dosage unit comprises a compressed or molded tablet, wherein each of the tablets within the capsule provides a different drug release profile. That is, for an exemplary dosage form, a first tablet releases drug substantially immediately following ingestion of the dosage form, while a second tablet in the capsule releases drug approximately 3–5 hours following ingestion, and an optional third tablet provides drug release after approximately 7–9 hours. While the dosage form will not generally include more than three tablets, dosage forms housing four or more tablets are within the scope of the present invention.

In an alternative embodiment, each dosage unit comprises a drug-containing particle or bead (drug-containing "beads" refer to drug-coated inert supports, e.g., lactose beads coated with drug). A first group of these particles or beads releases drug substantially immediately following ingestion of the dosage form, a second group releases drug approximately 3–5 hours following ingestion, and an optional third group provides drug release after approximately 7–9 hours.

In a further alternative embodiment, the individual dosage units are compacted in a single tablet, and represent integral but discrete segments thereof (e.g., layers). For example, drug-containing particles or drug-containing beads can be compressed together into a single tablet using conventional tabletting means.

As will be appreciated by those skilled in the art and as described in the pertinent texts and literature, a number of methods are available for preparing drug-containing tablets or other dosage units which provide a variety of drug release profiles. Such methods include coating a drug or drug-containing composition, increasing the drug's particle size, placing the drug within a matrix, and forming complexes of the drug with a suitable complexing agent.

The delayed release dosage units in the present capsules can be prepared, for example, by coating a drug or a drug-containing composition with a selected membrane coating material, typically although not necessarily a polymeric material. When a coating is used to provide delayed release dosage units, particularly preferred coating materials comprise bioerodible, gradually hydrolyzable and/or gradually water-soluble polymers. The "coating weight," or relative amount of coating material per dosage unit, generally dictates the time interval between ingestion and drug release.

Suitable membrane coating materials for effecting delayed release include, but are not limited to: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, cellulose ester-ether phthalate, hydroxypropylcellulose phthalate, alkali salts of cellulose acetate phthalate, alkaline earth salts of cellulose acetate phthalate, hydroxypropylmethyl cellulose hexahydrophthalate, cellulose acetate hexahydrophthalate, and carboxymethylcellulose sodium; acrylic acid polymers and copolymers preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, with a terpolymer of ethyl acrylate, methyl methacrylate and trimethylammonioethyl methacrylate chloride (sold under the tradename Eudragit RS) particularly preferred; vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac, ammoniated shellac, shellac-acetyl alcohol, and shellac n-butyl stearate.

In some cases, it may be desirable for the third tablet or bead or particle fraction to provide for release of the active agent in the colon, in which case polymeric or other materials are used that enable drug release within the colon. These may be selected from the aforementioned list, or other materials may be used as will be known to those skilled in the art of pharmaceutical formulation and drug delivery. For example, hydrocolloid gums may be effective to provide for colonic delivery, e.g., guar gum, locust gum, bena gum, gum tragacanth, and karaya gum (see, e.g., U.S. Pat. No. 5,656, 294 to Friend). Other materials suitable for effecting colonic drug delivery include polysaccharides, mucopolysaccharides, and related compounds, e.g., pectin, arabinogalactose, chitosan, chondroitin sulfate, dextran, galactomannan, and xylan.

Combinations of different coating materials may also be used to coat a single dosage unit.

To bring about the desired pulsatile release profile for a dosage form comprised of encapsulated tablets, the first tablet is provided with little or no coating material, the second tablet is provided with some degree of coating material, the coating weight of a third tablet is still higher, and so on. Analogously, for encapsulated dosage forms in which the drug-containing dosage units are beads or particles, a first fraction of beads or particles is provided with little or no coating material, a second fraction is provided with some degree of coating material, the coating weight of a third fraction is still higher, etc. For example, when the dosage form contains three tablets (or, analogously, three groups of drug-containing particles or beads), the first tablet, which releases drug substantially immediately, may have a total coating weight of less than about 10%, preferably less than about 8%, the second tablet may have a total coating weight in the range of approximately 10% to 30%, preferably 15% to 25%, and the third tablet, if present, may have a total coating weight in the range of approximately 15% to 65%, preferably 20% to 65%. The preferred coating weights for particular coating materials may be readily determined by those skilled in the art by evaluating individual release profiles for dosage units prepared with different quantities of various coating materials.

Alternatively, the delayed release dosage units, i.e., tablets or particles, may be formulated by dispersing the drug within a matrix of a suitable material such as an insoluble plastic, a hydrophilic polymer, or a fatty compound. The insoluble plastic matrices may be comprised of, for example, polyvinyl chloride or polyethylene. Hydrophilic polymers useful for providing a matrix for a delayed release dosage unit include, but are not limited to, those described above as suitable coating materials. Fatty compounds for use as a matrix material include, but are not limited to, waxes generally (e.g., carnauba wax) and glyceryl tristearate. Once the active ingredient is mixed with the matrix material, the mixture can be compressed into tablets or processed into individual drug-containing particles.

The individual dosage units may be provided with colored coatings, with a single color used to identify a tablet or bead or particle fraction having a corresponding delayed release profile. That is, for example, a blue coating may be used for the immediate release tablet or bead or particle fraction, a red coating may be used for the "medium" release tablet or bead or particle fraction, and the like. In this way, errors during manufacture can be easily avoided. The color is introduced by incorporating a pharmaceutically acceptable colorant into the coating during coating preparation. The colorant may be either natural or synthetic. Natural colorants include pigments such as chlorophyll, anattenes, beta-carotene, alizarin, indigo, rutin, hesperidin, quercitin, carminic acid, and 6,6'-dibromoindigo. Synthetic colorants are dyes, including both acidic dyes and basic dyes, such as nitroso dyes, nitro dyes, azo dyes, oxazines, thiazines, pyrazolones, xanthenes, indigoids, anthraquinones, acridines, rosanilines, phthaleins, quinolines. e.g., a dye or pigment, during preparation of the coating solution.

For encapsulated tablets, the weight of each individual tablet in the capsule is typically in the range of about 10 mg to 150 mg, preferably in the range of about 25 mg to about 100 mg, and most preferably is in the range of about 40 mg to 80 mg. The individual tablets are prepared using conventional means. A preferred method for forming tablets herein is by direct compression of a powdered, crystalline or granular drug-containing composition, alone or in combination with diluents, binders, lubricants, disintegrants, colorants or the like. As an alternative to direct compression, compressed tablets can be prepared using wet-granulation or dry-granulation processes. Tablets may also be molded rather than compressed, starting with a moist material containing a suitable water-soluble lubricant. Preferred tablets herein are manufactured using compression rather than molding, however. Drug-containing particles or beads are also prepared using conventional means, typically from a fluid dispersion.

Conventional coating procedures and equipment may then be used to coat the dosage units, i.e., the drug-containing tablets, beads or particles. For example, a delayed release coating composition may be applied using a coating pan, an airless spray technique, fluidized bed coating equipment, or the like. For detailed information concerning materials, equipment and processes for preparing tablets, beads, drug particles, and delayed release dosage forms, reference may be had to *Pharmaceutical Dosage Forms: Tablets,* eds. Lieberman et al. (New York: Marcel Dekker, Inc., 1989), and to Ansel et al., *Pharmaceutical Dosage Forms and Drug Delivery Systems,* 6$^{th}$ Ed. (Media, Pa.: Williams & Wilkins, 1995).

Optional components present in the individual drug-containing dosage units include, but are not limited to, diluents, binders, lubricants, disintegrants, stabilizers, surfactants, coloring agents, and the like. Diluents, also termed "fillers," are typically necessary to increase the bulk of a tablet so that a practical size is provided for compression. Suitable diluents include, for example, dicalcium phosphate dihydrate, calcium sulfate, lactose, cellulose, kaolin, mannitol, sodium chloride, dry starch, hydrolyzed starches, silicon dioxide, titanium oxide, alumina, talc, microcrystalline cellulose, and powdered sugar. Binders are used to impart cohesive qualities to a tablet formulation, and thus ensure that a tablet remains intact after compression. Suitable binder materials include, but are not limited to, starch (including corn starch and pregelatinized starch), gelatin, sugars (including sucrose, glucose, dextrose, lactose and sorbitol), polyethylene glycol, waxes, natural and synthetic gums, e.g., acacia, tragacanth, sodium alginate, polyvinylpyrrolidone, celluloses, and Veegum, and synthetic polymers such as polymethacrylates and polyvinylpyrrolidone. Lubricants are used to facilitate tablet manufacture; examples of suitable lubricants include, for example, magnesium stearate, calcium stearate, stearic acid, glyceryl behenate, and polyethylene glycol, and are preferably present at no more than approximately 1 wt. % relative to tablet weight. Disintegrants are used to facilitate tablet disintegration or "breakup" after administration, and are generally starches, clays, celluloses, algins, gums or crosslinked polymers. Stabilizers are used to inhibit or retard drug decomposition reactions which include, by way of example, oxidative reactions. Surfactants may be anionic, cationic, amphoteric or nonionic surface active agents, with anionic surfactants preferred. Suitable anionic surfactants include, but are not limited to, those containing carboxylate, sulfonate and sulfate ions, associated with cations such as sodium, potassium and ammonium ions. Particularly preferred surfactants include, but are not limited to: long alkyl chain sulfonates and alkyl aryl sulfonates such as sodium dodecylbenzene sulfonate; dialkyl sodium sulfosuccinates, such as sodium bis-(2-ethylhexyl)-sulfosuccinate; and alkyl sulfates such as sodium lauryl sulfate. If desired, the tablets may also contain minor amounts of nontoxic auxiliary substances such as wetting or emulsifying agents, pH buffering agents, preservatives, and the like.

As noted earlier herein, the individual drug tablets, beads or particles are, in one embodiment, contained within a closed capsule. The capsule material may be either hard or soft, and as will be appreciated by those skilled in the art of pharmaceutical science, typically comprises a tasteless, easily administered and water soluble compound such as gelatin, starch or cellulose. A preferred capsule material is gelatin. The capsules are preferably sealed, such as with gelatin bands or the like. See, for example, *Remington: The Science and Practice of Pharmacy,* Nineteenth Edition (Easton, Pa.: Mack Publishing Co., 1995), which describes materials and methods for preparing encapsulated pharmaceuticals designed to dissolve shortly after ingestion.

The novel dosage forms are used to administer methylphenidate in a pulsatile release manner. As noted earlier herein, the drug is administered as a racemic mixture of the d-threo and l-threo enantiomers. For administration of racemic methylphenidate, a dosage form of the invention comprises a total of approximately 2 mg to 100 mg methylphenidate, preferably 2 mg to 50 mg methylphenidate, divided among the individual dosage units. Optimally, the first and second dosage units each contain approximately 2 mg to 20 mg methylphenidate, and preferably, the first and second methylphenidate doses are approximately the same. The third tablet should contain a lower dose of methylphenidate, preferably about half the dose in the first tablet, to avoid sleep disruption. Also, if an additional CNS stimulant such as d-amphetamine is incorporated into the dosage form, it will be included in the first, immediate release dosage unit, will optionally be present in the second dosage unit, (and if present, at a lower dose than in the first dosage unit), and will not be included in the third dosage unit.

It may be desirable to include one or more additional active agents in the dosage forms herein. These active agents may potentiate certain effects of methylphenidate, or vice versa. The additional active agent or agents may be combined with methylphenidate in a single dosage unit within the dosage form, or one or more dosage units within the dosage form may comprise the additional active agent without any methylphenidate. In the former case, the various active agents may be present as an admixture in a tablet, or the agents may be physically segregated as in a bilayer tablet, a tablet having two or more active agent-containing coatings, or the like.

Preferred additional active agents, i.e., active agents for co-administration with methylphenidate, are CNS stimulants (including analeptic agents and psychostimulants), antidepressant drugs and antianxiety agents. Particularly preferred are CNS stimulants including, but not limited to: amphetamine (racemic), d-amphetamine, amphetamine and d-amphetamine phosphate, amphetamine and d-amphetamine sulfate, amphetamine and d-amphetamine hydrochloride, amphetamine and d-amphetamine saccharate, and amphetamine and d-amphetamine aspartate, amphetaminil, bemegride, benzphetamine, benzphetamine hydrochloride, brucine, chlorphentermine, clofenciclan, clortermine, deanol acetamidobenzoate, demanyl phosphate, dexoxadrol, diethpropion, doxapram hydrochloride, N-ethylamphetamine, ethamivan, etifelmin, etryptamine, fencamfamine, fenethylline, fenosolone, fenfluramine, flurothyl, hexacyclonate sodium, homocamfin, mazindol, megexamide, methamphetamine, nicotinic agonists, nikethamide, pemoline, pentylenetetrazole, phenidimetrazine, phendimetrazine tartrate, phenmetrazine, phenmetrazine hydrochloride, phentermine, picrotoxin, pipradrol, pipradrol hydrochloride, prolintane, pyrovalerone, racephedrine, racephedrine hydrochloride, and tetrahydrobenzothienopyridines. Pemoline, amphetamine, d-amphetamine and salts thereof are particularly preferred additional active agents.

Antidepressant drugs include, for example: tricyclic antidepressants such as imipramine, amitryptyline, amoxapine, clomipramine, desipramine, doxepin, imipramine, maprotiline, nortriptyline, protriptyline and trimipramine; monoamine oxidase inhibitors (MAOIs) such as isocarboxazid, phenelzine, selegiline and tranylcypromine; selective serotonin reuptake inhibitors (SSRIs) such as fluoxetine, fluvoxamine, paroxetine, sertraline, venlaxafine, and the like; and other antidepressants including buproprion, nefazodone and trazodone.

Examples of antianxiety agents include, but are not limited to, benzodiazepines such as alprazolam, chlordiazepoxide, clonazepam, clorazepate, diazepam, estazolam, flurazepam, halazepam, lorazepam, midazolam, oxazepam, prazepam, quazepam, temazepam and triazolam; carbamates such as meprobamate and ethinamate; chloral hydrate and related drugs; piperidine-diones such as glutethimide and methyprylon; alcohols such as ethchlorvynol; antihistaminics such as diphenhydramine and hydroxyzine; methaqualone; and paraldehyde.

Each of the active agents in the individual tablets may be in the form of a pharmaceutically acceptable salt, ester, amide, prodrug or other derivative or analog, including active agents modified by appending one or more appropriate functionalities to enhance selected biological properties. Such modifications are known in the art and/or are described in the pertinent texts and literature.

Salts of the active agents used in conjunction with the present dosage forms may be obtained commercially or can be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992). Suitable acids for preparing acid addition salts may be weak acids, medium acids, or strong acids, and include both organic acids, e.g., acetic acid, propionic acid, glycolic acid, pyruvic acid, oxalic acid, malic acid, malonic acid, succinic acid, maleic acid, fumaric acid, aspartic acid, saccharic acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. Preparation of basic salts of acid moieties which may be present (e.g., carboxylic acid groups) are prepared using a pharmaceutically acceptable base such as sodium hydroxide, potassium hydroxide, ammonium hydroxide, calcium hydroxide, magnesium hydroxide, trimethylamine, or the like. Preparation of esters involves functionalization of hydroxyl and/or carboxyl groups which may be present. These esters are typically acyl-substituted derivatives of free alcohol groups, i.e., moieties which are derived from carboxylic acids of the formula RCOOH where R is alkyl, and preferably is lower alkyl. Pharmaceutically acceptable esters may be prepared using methods known to those skilled in the art and/or described in the pertinent literature. Amides, prodrugs, and other analogs and derivatives can be readily prepared as well, using conventional means.

Utility

The novel drug dosage forms are to be administered orally to a mammalian individual and can be used to administer methylphenidate to treat or prevent a variety of disorders, conditions and diseases. In accordance with the present invention, administration of methylphenidate may be carried out in order to treat any disorder, condition or disease for which methylphenidate is generally indicated. Such disorders, conditions and diseases include, for example, ADD, ADHD, narcolepsy, and acute depression; methylphenidate may also be used in the treatment of individuals suffering from cognitive decline associated with AIDS or AIDS-related conditions, and for mood elevation in terminally ill patients suffering from a disease such as cancer.

For administration of racemic methylphenidate, the typical daily dose is in the range of approximately 5 mg to 100 mg, preferably 5 mg to 60 mg, although the exact dosage regimen will depend on a number of factors, including age, the general condition of the patient, the particular condition or disorder being treated, the severity of the patient's condition or disorder, and the like.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

Experimental

The practice of the present invention will employ, unless otherwise indicated, conventional techniques of pharmaceutical formulation, medicinal chemistry, biological testing, and the like, which are within the skill of the art. Such techniques are explained fully in the literature. Preparation of various types of pharmaceutical formulations are described, for example, in Lieberman et al., cited supra; synthesis of chiral drugs is described, inter alia, in Wilson and Gisvold, *Textbook of Organic, Medicinal and Pharmaceutical Chemistry* (Lippincott-Raven Publishers, 1991); and Gibaldi and Perrier, *Pharmacokinetics* (Marcel Dekker, 1982), provides a description of the biological testing procedures useful to evaluate compounds such as those described and claimed herein. All patents, patent applications, and publications mentioned herein, both supra and infra, are hereby incorporated by reference.

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric. All reagents were obtained commercially unless otherwise indicated.

EXAMPLE 1

Pulsatile Delivery System for Oral Administration of d,l-Threo Methylphenidate

A pulsatile release dosage form for administration of d,l-threo methylphenidate is prepared by (1) formulating three individual compressed tablets, each having a different release profile, followed by (2) encapsulating the three tablets into a gelatin capsule and then closing and sealing the capsule. The components of the three tablets are as follows.

TABLET 1 (IMMEDIATE RELEASE):

| Component | Function | Amount per tablet |
|---|---|---|
| d,l-threo methylphenidate | Active agent | 5.0 mg |
| Dicalcium phosphate dihydrate | Diluent | 26.6 mg |
| Microcrystalline cellulose | Diluent | 26.6 mg |
| Sodium starch glycolate | Disintegrant | 1.2 mg |
| Magnesium Stearate | Lubricant | 0.6 mg |

TABLET 1A (IMMEDIATE RELEASE):

| Component | Function | Amount per tablet |
|---|---|---|
| d,l-threo methylphenidate | Active agent | 2.5 mg |
| Dicalcium phosphate dihydrate | Diluent | 26.6 mg |
| Microcrystalline cellulose | Diluent | 26.6 mg |
| Sodium starch glycolate | Disintegrant | 1.2 mg |
| Magnesium Stearate | Lubricant | 0.6 mg |

TABLET 2 (RELEASE DELAYED 3–5 HOURS FOLLOWING ADMINISTRATION):

| Component | Function | Weight |
|---|---|---|
| Tablet 1 | "Core" containing the active agent | 60.0 mg |
| Eudragit RS30D | Delayed release coating material | 4.76 mg |
| Talc | Coating component | 3.3 mg |
| Triethyl citrate | Coating component | 0.95 mg |

TABLET 3 (RELEASE DELAYED 7–9 HOURS FOLLOWING ADMINISTRATION):

| Component | Function | Weight |
|---|---|---|
| Tablet 1A | "Core" containing the active agent | 57.5 mg |
| Eudragit RS30D | Delayed release coating material | 6.34 mg |
| Talc | Coating component | 4.4 mg |
| Triethyl citrate | Coating component | 1.27 mg |

The tablets are prepared by wet granulation of the individual drug particles and other core components as may be done using a fluid-bed granulator, or are prepared by direct compression of the admixture of components. Tablet 1 is an immediate release dosage form, releasing the active agent within 1–2 hours following administration. Tablets 2 and 3, after this initial preparation, are coated with the delayed release coating material as may be carried out using conventional coating techniques such as spray-coating or the like. As will be appreciated by those skilled in the art, the specific components listed in the above tables may be replaced with other functionally equivalent components, e.g., diluents, binders, lubricants, fillers, coatings, and the like.

Oral administration of the capsule to a patient will result in a release profile having three pulses, with initial release of the methylphenidate from the first tablet being substantially immediate, release of the methylphenidate from the second tablet occurring 3–5 hours following administration, and release of the methylphenidate from the third tablet occurring 7–9 hours following administration. Because Tablet 3 contains a lower dosage of methylphenidate than Tablets 1 or 2, the likelihood of sleep disruption is substantially reduced.

EXAMPLE 2

The method of Example 1 is repeated, except that drug-containing beads are used in place of tablets. A first fraction of beads may be prepared by coating an inert support material such as lactose with the drug which provides the first (immediate release) pulse. A second fraction of beads is prepared by coating immediate release beads with an amount of enteric coating material sufficient to provide a drug release-free period of 3–5 hours. A third fraction of beads is prepared by coating immediate release beads having half the methylphenidate dose of the first fraction of beads with a greater amount of enteric coating material, sufficient to provide a drug release-free period of 7–9 hours. The three groups of beads may be encapsulated as in Example 1, or compressed, in the presence of a cushioning agent, into a single pulsatile release tablet.

Alternatively, three groups of drug particles may be provided and coated as above, in lieu of the drug-coated lactose beads.

What is claimed is:

1. A pulsatile release dosage form for oral administration of methylphenidate and an additional drug, comprising an immediate release dosage unit and a delayed release dosage unit, wherein following oral ingestion of the dosage form by a patient, a first dose of methylphenidate is released substantially immediately from the immediate release dosage unit, followed by a time interval during which substantially no drug is released from the dosage form, and after which time interval a second dose of methylphenidate is released from the delayed release dosage unit, and further wherein the dosage form additionally comprises a dose of the additional drug.

2. The dosage form of claim 1, wherein the additional drug is contained in the immediate release dosage unit.

3. The dosage form of claim 1, wherein the additional drug is contained in the delayed release dosage unit.

4. The dosage form of claim 2, wherein the additional drug is also contained in the delayed release dosage unit.

5. The dosage form of claim 2, wherein the additional drug and the methylphenidate are present as an admixture in the immediate release dosage unit.

6. The dosage form of claim 2, wherein the additional drug and the methylphenidate are physically segregated within the immediate release dosage unit.

7. The dosage form of claim 3, wherein the additional drug and the methylphenidate are present as an admixture in the delayed release dosage unit.

8. The dosage form of claim 3, wherein the additional drug and the methylphenidate are physically segregated within the delayed release dosage unit.

9. The dosage form of claim 1, wherein the additional drug is present in a third dosage unit within the dosage form.

10. The dosage form of claim 1, wherein the first dose of methylphenidate is released within 2 hours of ingestion and the second dose of methylphenidate is released approximately 3 to 5 hours after ingestion.

11. The dosage form of claim 1, wherein the dosage form is a capsule and the immediate release and delayed release dosage units are tablets contained therein.

12. The dosage form of claim 1, wherein the immediate release dosage unit is comprised of a plurality of beads or particles together containing the first dose of methylphenidate, and the delayed release dosage unit is comprised of a plurality of beads or particles together containing the second dose of methylphenidate.

13. The dosage form of claim 1, wherein a second time interval follows release of the second dose of methylphenidate, and the dosage form further comprises an additional delayed release dosage unit that releases a third dose of methylphenidate, a dose of the additional drug, or both, after the second time interval.

14. The dosage form of claim 13, wherein the first dose of methylphenidate is released within 1 hour of ingestion, the second dose of methylphenidate is released approximately 3 to 5 hours after ingestion, and the third dose of methylphenidate, the dose of the additional drug, or both, are released approximately 7 to 9 hours after ingestion.

15. The dosage form of claim 1, wherein the total methylphenidate in the dosage form is in the range of approximately 2 mg to 100 mg.

16. The dosage form of claim 13, wherein the total methylphenidate in the dosage form is in the range of approximately 2 mg to 50 mg.

17. The dosage form of claim 1, wherein the first dose of methylphenidate and the second dose of methylphenidate are each in the range of approximately 2 mg to 20 mg.

18. The dosage form of claim 1, wherein the methylphenidate is a racemic mixture of D-threo methylphenidate and L-threo methylphenidate.

19. The dosage of claim 1, wherein the methylphenidate is enantiomerically pure D-threo methylphenidate.

20. The dosage form of claim 1, wherein the methylphenidate in each dosage unit comprises approximately 55% to 95% D-threo methylphenidate and approximately 45% to 5% L-threo methylphenidate.

21. The dosage form of claim 1, wherein the methylphenidate in each dosage unit comprises 75% to 95% D-threo methylphenidate and 25% to 5% L-threo methylphenidate.

22. The dosage form of claim 1, wherein the additional drug is a CNS stimulant.

23. The dosage form of claim 22, wherein the additional drug is an analeptic agent.

24. The dosage form of claim 22, wherein the CNS stimulant is selected from the group consisting of amphetamine, d-amphetamine, amphetaminil, bemegride, benzphetamine, brucine, chlorphentermine, clofenciclan, clortermine, deanol acetamidobenzoate, demanyl, dexoxadrol, diethpropion, doxapram, N-ethylamphetamine, ethamivan, etifelmin, etryptamine, fencamfamine, fenethylline, fenosolone, fenfluramine, flurothyl, hexacyclonate, homocamfin, mazindol, megexamide, methamphetamine, nicotinic agonists, nikethamide, pemoline, pentylenetetrazole, phenidimetrazine, phenmetrazine, phentermine, picrotoxin, pipradrol, prolintane, pyrovalerone, racephedrine, tetrahydrobenzothienopyridines, and pharmacologically acceptable salts thereof.

25. The dosage form of claim 24, wherein the CNS stimulant is selected from the group consisting of amphetamine, d-amphetamine, and pharmacologically acceptable salts thereof.

26. The dosage form of claim 25, wherein the CNS stimulant is selected from the group consisting of amphetamine, d-amphetamine, amphetamine phosphate, d-amphetamine phosphate, amphetamine sulfate, d-amphetamine sulfate, amphetamine hydrochloride, d-amphetamine hydrochloride, amphetamine saccharate, d-amphetamine saccharate, amphetamine aspartate, d-amphetamine aspartate, and combinations thereof.

27. The dosage form of claim 24, wherein the CNS stimulant is pemoline.

28. The dosage form of claim 1, wherein the additional drug is an antidepressant drug.

29. The dosage form of claim 28, wherein the antidepressant drug is selected from the group consisting of tricyclic antidepressants, monoamine oxidase inhibitors, selective serotonin reuptake inhibitors, buproprion, nefazodone, and trazodone.

30. The dosage form of claim 29, wherein the antidepressant drug is selected from the group consisting of amitryptyline, amoxapine, clomipramine, desipramine, doxepin, imipramine, maprotiline, nortriptyline, protriptyline and trimipramine, isocarboxazid, phenelzine, selegiline, tranylcypromine, fluoxetine, fluvoxamine, paroxetine, sertraline, venlaxafine, buproprion, nefazodone and trazodone.

31. The dosage form of claim 28, wherein the antidepressant drug is a selective serotonin reuptake inhibitor.

32. The dosage form of claim 1, wherein the additional drug is an antianxiety agent.

33. The dosage form of claim 32, wherein the antianxiety agent is selected from the group consisting of alprazolam, chiordiazepoxide, clonazepam, clorazepate, diazepam, estazolam, flurazepam, halazepam, lorazepam, midazolam, oxazepam, prazepam, quazepam, temazepam, triazolam, meprobamate, ethinamate, chloral hydrate, glutethimide, methyprylon, ethchlorvynol, diphenhydramine, hydroxyzine, methaqualone, and paraldehyde.

34. The dosage form of claim 1, wherein the sustained release dosage unit is provided with a coating of a delayed release membrane material.

35. The dosage form of claim 34, wherein the delayed release membrane material is comprised of a bioerodible, hydrolyzable and/or gradually water-soluble polymer.

36. The dosage form of claim 35, wherein the delayed release membrane material is an acrylic resin.

37. The dosage form of claim 36, wherein the delayed release membrane material is a copolymer of acrylic acid, methacrylic acid, methyl acrylate, ethyl acrylate, methyl methacrylate, ethyl methacrylate, and/or derivatives thereof.

38. The dosage form of claim 36, wherein the delayed release membrane material is a terpolymer of ethyl acrylate, methyl methacrylate and trimethylammonioethyl methacrylate chloride.

39. The dosage form of claim 1, wherein each dosage unit has a different color.

40. A method for treating an individual suffering from ADD, comprising administering to the individual, once daily, the dosage form of claim 1.

41. A method for treating an individual suffering from ADHD, comprising administering to the individual, once daily, the dosage form of claim 1.

42. A method for treating an individual suffering from narcolepsy, comprising administering to the individual, once daily, the dosage form of claim 1.

43. A method for treating an individual suffering from acute depression, comprising administering to the individual, once daily, the dosage form of claim 1.

44. A method for treating an individual suffering from cognitive decline associated with Acquired Immunodeficiency Syndrome ("AIDS") or AIDS-related conditions, comprising administering to the individual, once daily, the dosage form of claim 1.

45. A method for elevating the mood of a terminally ill patient, comprising administering to the patient, once daily, the dosage form of claim 1.

* * * * *